US008425863B2

(12) United States Patent
Van Haag et al.

(10) Patent No.: US 8,425,863 B2

(45) Date of Patent: Apr. 23, 2013

(54) MICRO FLUIDIC DEVICE

(75) Inventors: Chris Van Haag, Eindhoven (NL); Ronald Cornelis De Gier, Eindhoven (NL); Adrianus Wilhelmus Dionisius Maria Van Den Brijgaart, Eindhoven (NL); Gheorghe Sorin Stan, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 273 days.

(21) Appl. No.: 12/519,373

(22) PCT Filed: Dec. 12, 2007

(86) PCT No.: PCT/IB2007/055045

§ 371 (c)(1),
(2), (4) Date: Jun. 16, 2009

(87) PCT Pub. No.: WO2008/075253

PCT Pub. Date: Jun. 26, 2008

(65) Prior Publication Data

US 2010/0104474 A1 Apr. 29, 2010

(30) Foreign Application Priority Data

Dec. 19, 2006 (EP) .................................... 06126466

(51) Int. Cl.
*G01N 33/00* (2006.01)

(52) U.S. Cl.
USPC .......... 422/537; 422/68.1; 422/502; 422/503; 422/504; 422/505; 422/538; 422/539; 422/540; 422/541; 137/334; 137/47; 137/223; 137/225; 251/12; 251/213; 251/331; 251/129.17

(58) Field of Classification Search .................. 422/104, 422/68.1, 100, 500–509, 537–541; 137/334, 137/47, 223, 225, 833; 251/12, 213, 331, 251/129.17

See application file for complete search history.

(56) References Cited

U.S. PATENT DOCUMENTS

| | | | | |
|---|---|---|---|---|
| 5,145,152 | A | 9/1992 | Komuro et al. | |
| 5,863,502 | A * | 1/1999 | Southgate et al. | 422/430 |
| 6,736,370 | B1 | 5/2004 | Crockett et al. | |
| 2003/0057391 | A1 | 3/2003 | Krulevitch et al. | |
| 2004/0209354 | A1 * | 10/2004 | Mathies et al. | 435/287.2 |
| 2004/0261850 | A1 | 12/2004 | Maula et al. | |
| 2005/0098749 | A1 | 5/2005 | Claydon et al. | |
| 2005/0238506 | A1 * | 10/2005 | Mescher et al. | 417/413.1 |

FOREIGN PATENT DOCUMENTS

| | | | |
|---|---|---|---|
| DE | 19534137 | A1 | 3/1997 |
| WO | 9509987 | A1 | 4/1995 |

* cited by examiner

*Primary Examiner* — In Suk Bullock
*Assistant Examiner* — Sharon Pregler

(57) ABSTRACT

A micro fluidic device includes a valve/pump-unit with reduced dead volume having a substrate. The lower surface of the substrate includes two micro channels spaced apart by a valve area of the substrate that separates the two micro channels. A flexible membrane is arranged on the lower surface of the substrate facing an actuating element located in a through going cut-out of a cover element. Movement of the actuating element towards and away from the valve area of the substrate causes a pump and/or valve action of the flexible membrane area, respectively, to cause or stop a directed fluid flow between the two micro channels through a channel formed between the valve area of the substrate and the flexible membrane.

18 Claims, 10 Drawing Sheets

MICRO FLUIDIC DEVICE

BACKGROUND OF THE INVENTION

1. Field of the Invention

This invention relates to a micro fluidic device comprising a valve/pump-unit. The micro fluidic device comprising said valve/pump-unit according to the present invention is preferably used in molecular diagnostics.

2. Background Art

The biotechnology sector has directed substantial effort towards developing miniaturized fluid sample transport devices such as microfluidic devices, often termed labs-on-a-chip (LOC) or micro total analyses systems (microTAS), for sample manipulation and analysis. These systems are used for detection and analyses of specific bio-molecules, such as DNA and proteins.

In general micro-system devices contain fluidic, electrical and mechanical functions, comprising pumps, valves, mixers, heaters, and sensors such as optical-, magnetic- and/or electrical sensors. A typical molecular diagnostic assay includes process steps such as cell lyses, washing, amplification by PCR, and/or detection.

Integrated microfluidic devices need to combine a number of functions, like filtering, mixing, fluid actuation, heating, cooling and optical, electrical or magnetic detection, on a single template. Following a modular concept the different functions can be realised on separate functional substrates, like silicon or glass. The functions need to be assembled with a microfluidic channel system, which is typically made of plastic. With small channel geometries this way of integration becomes a very challenging process. The interfaces between the substrates and the channel plate need to be very smooth and accurate, and the channel geometries need to be reproducible, while the functional substrates should have a minimum footprint for cost efficiency. Especially with functions, which need a fluidic as well as an electric interface, the separation of the wet interface is critical. Bonding techniques must be compatible with the biochemical reagents and surface treatments present on the functional substrates.

US-A1 2003/0057391, incorporated by reference, discloses a low power integrated pumping and valving array which provides a revolutionary approach for performing pumping and valving operations in micro fabricated fluidic systems for applications such as medical diagnostic microchips. This approach integrates a lower power, high-pressure source with a polymer, ceramic, or metal plug enclosed within a micro channel, analogous to a micro syringe. When the pressure source is activated, the polymer plug slides within the micro channel, pumping the fluid on the opposite side of the plug without allowing fluid to leak around the plug. The plugs also can serve as micro valves.

However, the pump system of US-A1 2003/0057391 does not provide a sufficient small dead volume and does not provide an optimized fast fluid transport. Further, the plugs must have a positive fitting to avoid sample fluid leakage thus the low power integrated pumping and valving arrays can not be provided at low vertical range of manufacture.

US 2005/0098749 discloses a micro valve and a method of forming a diaphragm stop for a micro valve. The micro valve includes a first layer and a diaphragm member to control the flow of fluid through the micro valve. The method comprises the step of forming a contoured shaped recess extending inward from a surface of the layer by using a laser to remove material in a series of areas, at successively greater depths extending inward from said surface. Preferably, the recess has a dome shape, and may be formed by a direct-write laser operated via a computer aided drawing program running on a computer. For example, CAD artwork files, comprising a set of concentric polygons approximating circles, may be generated to create the dome structure. Modifying the offset step distance of the polygons and equating certain line widths to an equivalent laser tool definition can control the laser ablation depth. Preferably, the laser tool definition is combined with the CAD artwork, which defines a laser path such that the resulting geometry has no sharp edges that could cause the diaphragm of the valve to tear or rupture.

US 2005/0098749 is directed to a micro valve only. Thus, the micro valve unit of US 2005/0098749 does not simultaneously integrate a pump as well as a valve function in the same unit. Further, the diaphragm member is not flexible so that the micro valve unit of US 2005/0098749 does not form and reform a temporally channel through which a fluid flow can be directed. As disclosed in US 2005/0098749 the diaphragm member opens a hole at a specific gas pressure so that the gas can pass through. However, the gas can not be pumped with the diaphragm member.

In the last decade, considerable research efforts have been made to the development pump-systems for microfluidic system devices in order to reducing the analyze samples volumes of liquid.

Despite this effort, there is still a need for a valve/pump-unit with an optimized reduced dead volume.

SUMMARY OF THE INVENTION

An object of the present invention is to provide a valve/pump-unit for a micro fluidic device.

The valve/pump-unit according of the present invention provides a fluid valve or pump action on a micro fluidic device with an optimized dead volume reduced to a minimum, preferably about zero.

This object is attained with a micro fluidic device comprising at least one valve/pump-unit, wherein the micro fluid device comprises:

a substrate, wherein on the lower surface of said substrate at least two micro channels are arranged to direct a fluid sample flow on the substrate, whereby said two micro channels are not end-to-end connected and spaced apart by a valve/pump-unit area of said substrate;

at least one flexible membrane, wherein the flexible membrane is arranged on the lower surface of said substrate;

an actuating element with an upper surface adjacent arranged to the flexible membrane;

at least one cover element arranged on the lower surface of the flexible membrane, wherein the cover element comprises at least one through going cut-out for receiving an actuating element, so that movement of said actuating element causes a pump and/or valve/pump-unit action of the adjacent arranged flexible membrane area to cause or stop a directed fluid flow on said substrate;

so that a fluid flow between said two not end-to-end connected micro channels is directed among the valve area of the lower surface of the substrate and the upper surface of the flexible membrane through a temporally formable channel formed by the flexible membrane covering the valve area, whereby a movement of the actuating element towards to the lower surface of the substrate causes a valve action and a movement opposite to the lower surface of the substrate releases space in a chamber into which the flexible membrane can engage to form the temporally channel and the upper surface of the actuating element covers at least partly the membrane surface at the valve area.

The valve/pump-unit according to the present invention simultaneously integrates a pump as well as a valve function in the same unit.

It can be preferred that the micro fluidic device comprises at least two valve/pump-units so that a fluid can for example be pumped bidirectional.

The micro fluidic device according to the present invention can be used to direct a fluid flow on a substrate to a desired area through a micro channel systems of permanent channels and temporally formed channels, whereby the fluid can be subjected to a relative low over pressure of for example 50 mbar to 1 bar, preferably 100 mbar to 300 mbar.

According to a preferred embodiment of the invention, the substrate comprises a plurality of micro channels and the sample fluid is directed from one micro channel to a plurality of micro channels via the valve area. Current techniques available allow running many reactions in parallel in different reaction chambers. The invention allows directing the sample fluid simultaneously to multiple reaction chambers via multiple micro channels by operating the valve/pump.

According to a further preferred embodiment of the invention, the valve area includes a fluid chamber, whereby the fluid chamber is arranged to store sample fluid. The sample fluid stored in the fluid chamber is dispensed to different reaction chambers via the micro channels. All the reaction chambers can be filled with the sample fluid at once by operating the valve/pump unit.

According to a further embodiment of the invention, the valve/pump is attached to a flexible foil, wherein the flexible foil is capable of aligning the valve/pump unit to the lower surface of the substrate when the actuating element is moved towards the lower surface of the substrate. This movement of the actuating element causes a fluid flow from the fluid chamber to the multiple not end-to-end connected micro channels. The flexible foil allows guiding of the valve/pump unit without restraining the alignment of the valve/pump unit to the substrate. In other words, the valve/pump unit can be actuated by one actuating element that pushes the valve/pump unit to the substrate closing the temporally formed channel. The flexible foil can be poly-propylene.

According to a still further embodiment of the invention, the micro channels are aligned radially and start from a bottom of the lower surface of the substrate from centre passing the valve area and crossing to a top of the lower surface of the substrate. This unique fluid channel design allows relatively simple sealing of the plurality of the micro channels with the flexible membrane that forms the lower surface of the fluid chamber. The flexible membrane closes all the micro channels with a movement of the actuating element towards to the lower surface of the substrate.

According to yet another embodiment of the invention, the flexible membrane is arranged to form a lower surface of the fluid chamber. The fluid flow is directed among the valve area of the lower surface of the substrate and the upper surface of the flexible membrane through a temporally formable channel formed by the flexible membrane covering the valve area, whereby a movement of the actuating element towards to the lower surface of the substrate causes a valve action and a movement opposite to the lower surface of the substrate releases space in a chamber into which the flexible membrane can engage to form the temporally channel and the upper surface of the actuating element covers at least partly the membrane surface at the valve area.

As used herein, the term “detection means” or “detecting element” refers to any means, structure or configuration, which allows one to interrogate a fluid sample within the sample-processing compartment using analytical detection techniques well known in the art. Thus, a detection means may include one or more apertures, elongated apertures or grooves which communicate with the sample processing compartment and may allow an external detection apparatus or device to be interfaced with the sample processing compartment to detect a fluid sample, also referred as analyte, passing through the fluid sample transport device.

The term “fluid sample” is used to refer to any compound or composition, which can be pumped through the temporally formed channel system. The “fluid sample” is preferably a liquid.

The term “channel” or “channel system” as used in the present invention means a conduit through which a fluid flow can be directed, for example to a desired cavity, recess and/or area located on the substrate.

The term “valve area” as used in the present invention means the surface area on the substrate located between at least two non end-to-end connected micro channels along which a fluid sample flow is possible through a temporally formed membrane channel only.

A channel or channel system can be connected with at least one cavity, recess and/or area located on the substrate where the fluid can be for example processed, collected, controlled and/or detected.

A temporally channel is formed by expanding or stretching the flexible membrane, so that the flexible membrane forms for a example a curve like tunnel on the substrate through that a fluid sample can flow.

The term “temporally” means with respect to the channel, that the channel is not permanent formed. This means that a temporally formed membrane channel can be reformed to a non-channel design, such as a planar or flat membrane design contacting the substrate.

The term “flexible” as used in the present invention with respect to the membrane means that the membrane is stretchable and elastic.

The terms “through going hole” and “through going cut” with respect to the cover element means that the through hole as well as the through cut extend from the upper surface of the cover element to the lower surface of the cover element (from one side to the other side).

The valve/pump-unit according to the present invention can be used on Lab-on-chip (LOC) or Micro Total Analyses Systems (micro TAS) in for example molecular diagnostics applications.

It can be seen from FIGS. 1 to 7 that the valve/pump unit is of a low vertical range of manufacture.

Another advantage is, that the actuating element needs not to be sealed liquid tight, since the fluid is sealed by the membrane already, so that the fluid flow is caused between the substrate comprising micro channels and the membrane surface arranged adjacent to the substrate.

A further advantage is that the valve/pump unit situated in the cover element does not contact the fluid sample. Thus, the cover element comprising the valve/pump unit is not contaminated with a fluid, e.g. fluid analyte sample, so that all parts can be reused except the substrate covered with the membrane.

Further benefits and advantages of the invention will become apparent from a consideration of the following detailed description, given with reference to the accompanying drawings, which specify and show preferred embodiments of the invention.

DETAILED DESCRIPTION OF THE PREFERRED EMBODIMENTS

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. Thus, for example, reference to "a fluid" may include mixtures, reference to "a device" includes two or more such devices, reference to "a unit" includes two or more such units, reference to "a temporally formed channel" may include more than at least one of such temporally formed channels, and the like.

Figure 1:
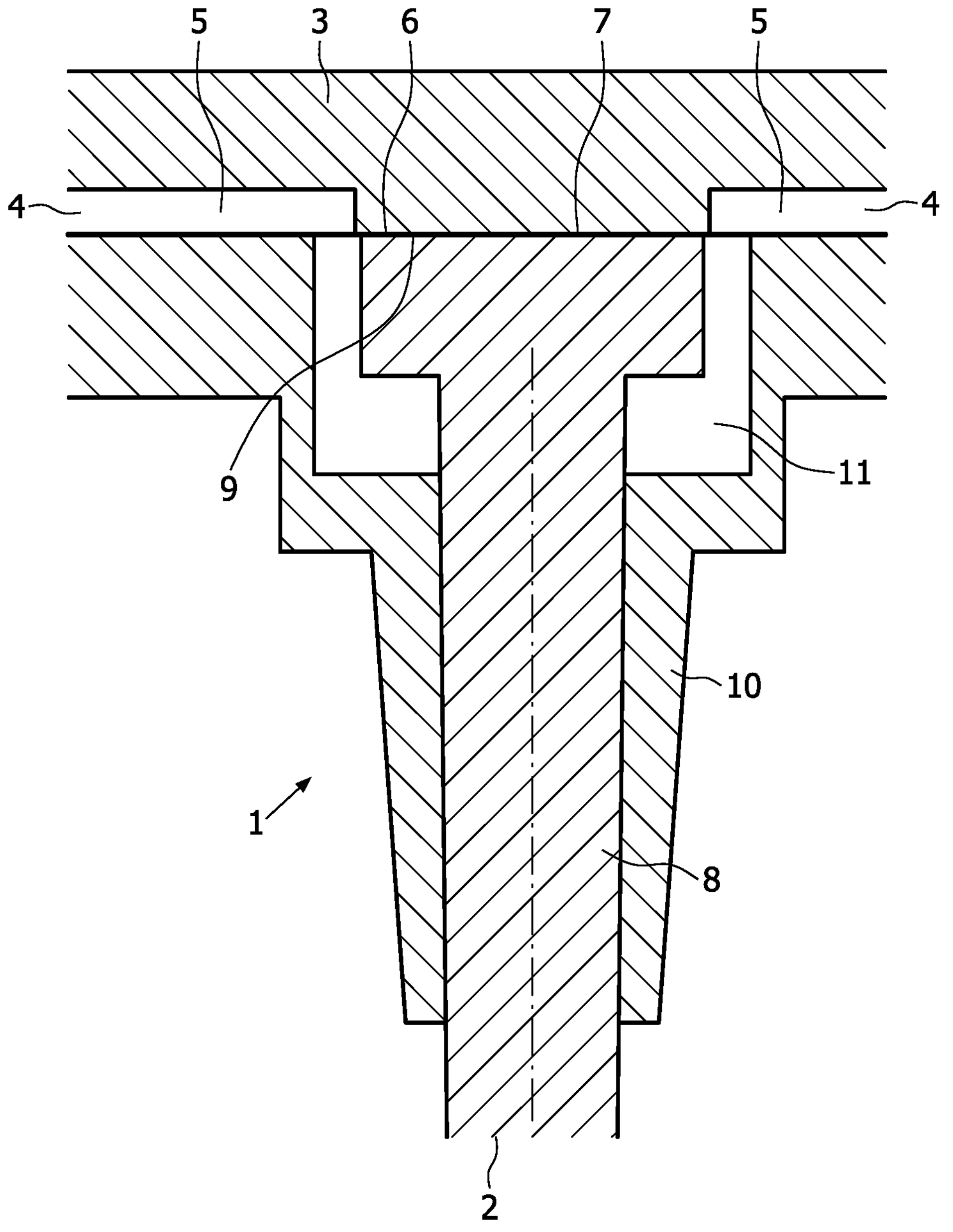
FIG. 1 is a sectional side view of a substrate with a closed valve of a valve/pump unit according to the present invention.

FIG. 1 shows in a sectional view a micro fluidic device 1 with a valve/pump-unit 2. The micro fluid device 1 comprises a substrate 3, wherein on the lower surface of said substrate 3 two micro channels 4 are arranged to direct a fluid sample 5 flow on the substrate 3, whereby said two micro channels 4 are not end-to-end connected and spaced apart by a valve area 6 of said substrate 3. Further, a flexible membrane 7 is arranged on the lower surface of said substrate 3 and sandwiched between the substrate and a cover element 10. The cover element 10 comprises a through going cut-out 11 for receiving an actuating element 8, wherein the upper surface 9 of the actuating element 8 is adjacent arranged to the flexible membrane 7, so that movement of said actuating element 8 causes a pump and/or valve action of the adjacent arranged flexible membrane section to cause or stop a directed fluid flow between said two not end-to-end connected micro channels 4 on said substrate 3. A movement of the actuating element 8 towards to the lower surface of the substrate 3 causes a valve action and a movement opposite to the lower surface of the substrate releases a space of a chamber 13 into which the flexible membrane 7 can engage to form a temporally channel 12. The upper surface 9 of the actuating element 8 covers exactly the outer surface of the valve area 6. Thus, the dead volume of the valve/pump unit 2 is about zero, since the upper surface 9 of the actuating element 8 covers exactly the outer surface of the valve area 6.

Figure 2:
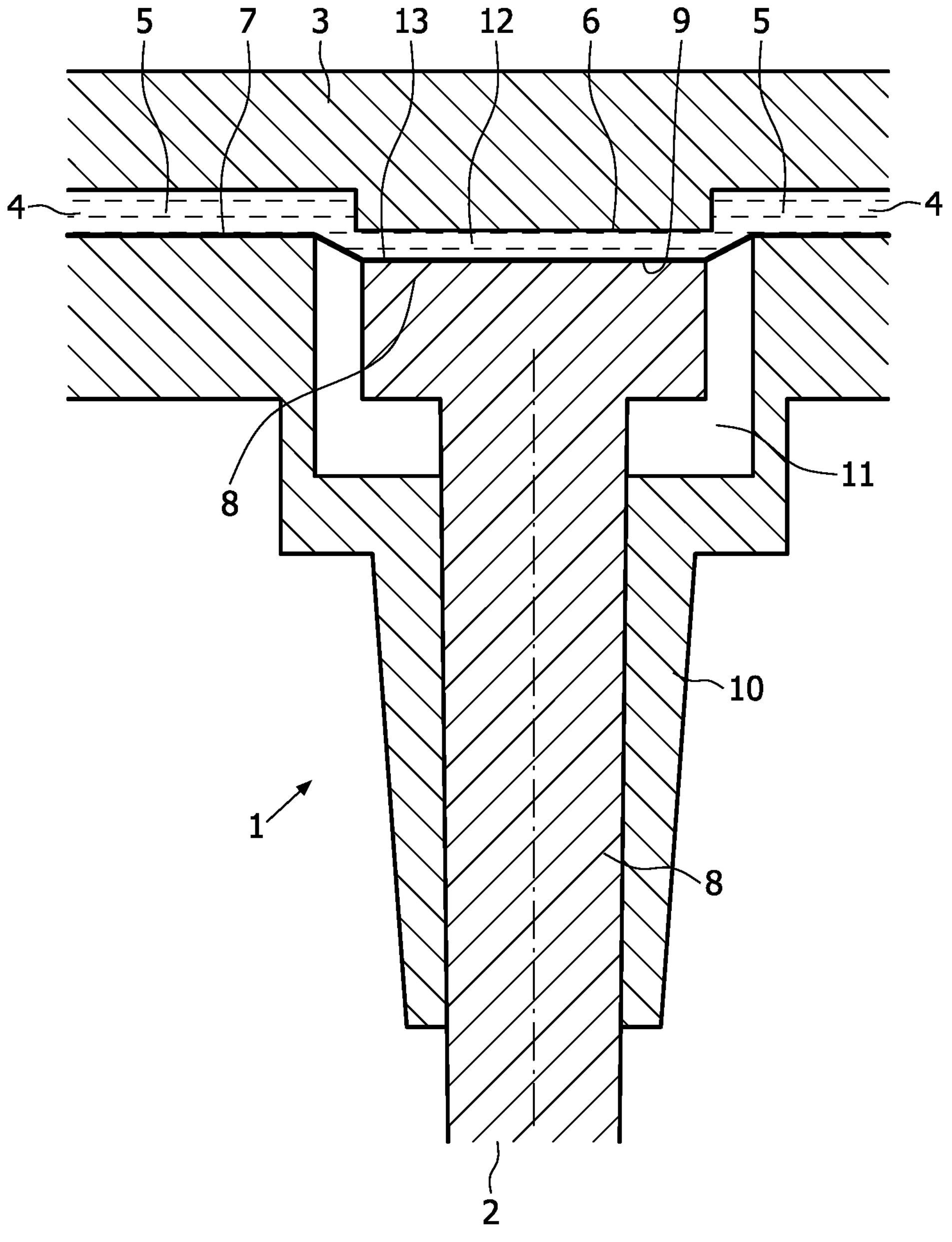
FIG. 2 is a sectional side view of a substrate with an open valve of a valve/pump unit according to the present invention and the membrane is mounted on the actuating element.

FIG. 2 shows a micro fluidic device 1 according to FIG. 1 wherein the valve/pump unit 2 is in an opened state. In a closed valve state, as can be seen in FIG. 1, the membrane below the surface of the actuating element 8 is pressed onto the substrate so that the fluid 5 is forced into the micro channel 4, so that no fluid 5 remains at the valve area 6 on the substrate 2. When opening the valve 2, as shown in FIG. 2, fluid 5 can flow into the temporally formed channel 12 along the valve area 6 from a first micro channel 4 to a second micro channel 4, whereby the channels 4 are disconnected by the valve area 6. According to the embodiment of FIG. 2, the membrane 7 is mounted to the upper surface 9 of the actuating element 8, so that a pump action to cause a fluid flow can be obtained by an up and down movement of the actuating element 8. In order to allow a directed fluid flow and/or to allow a forward and backward pumping of a fluid sample at least a second pump and/valve units 2 (not shown) is located on the fluidic device 1, wherein the at least two pump and/valve units are connected by a channel 4.

Figure 3:
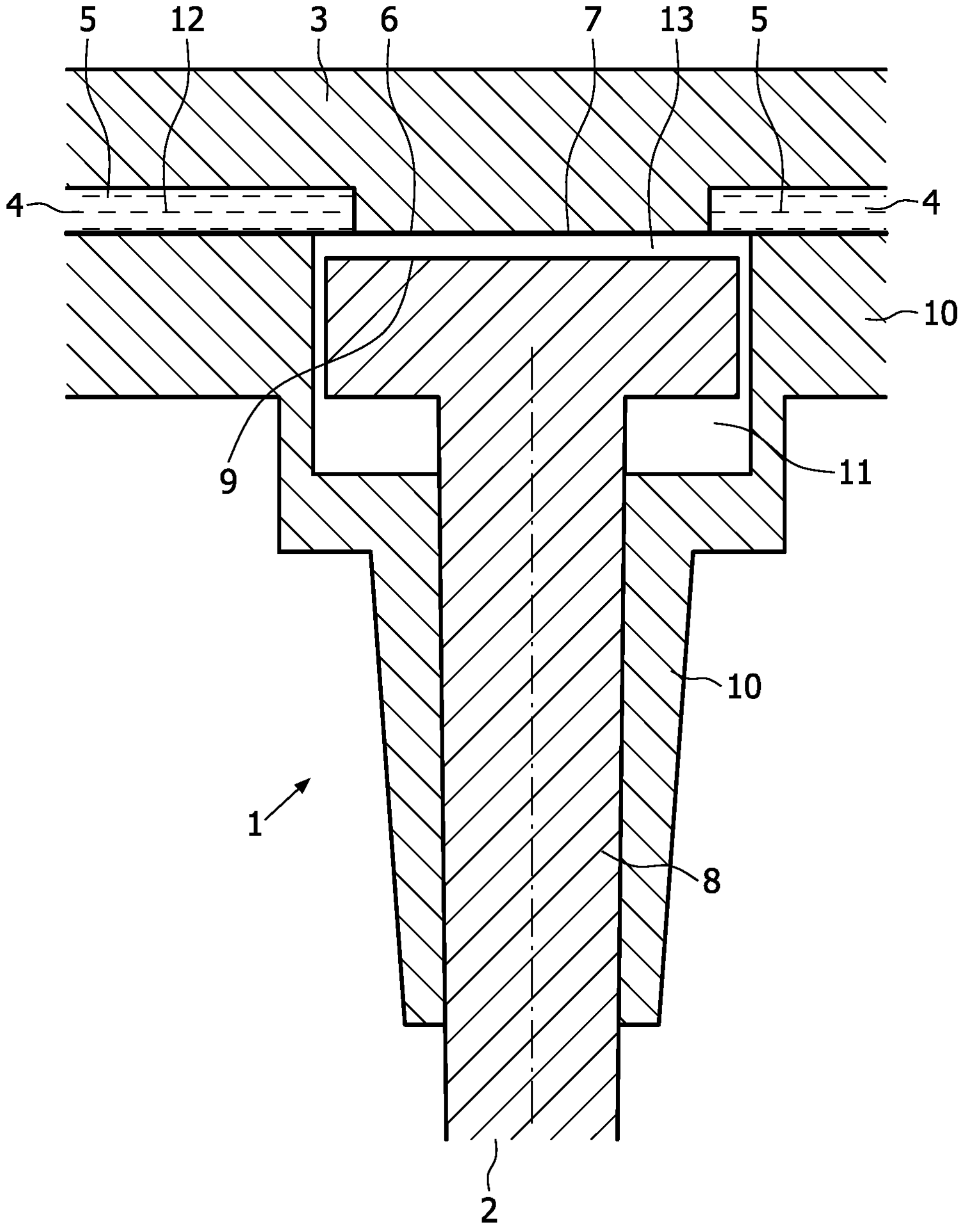
FIG. 3 is a sectional side view of a substrate with an open valve of a valve/pump unit according to the present invention and the membrane is not mounted on the actuating element.

FIG. 3 shows a micro fluidic device 1 according to FIG. 2 with the difference that the membrane 7 is not mounted to the upper surface 9 of the actuating element 8, so that the formation of a temporally channel 12 can be caused due to external pressure subjected to the fluid 5. However, closing the valve/pump unit 2 can cause a fluid flow with respect to the fluid 5 collected in the corresponding temporally formed channel 12 below the valve/pump unit 2.

Figure 4:
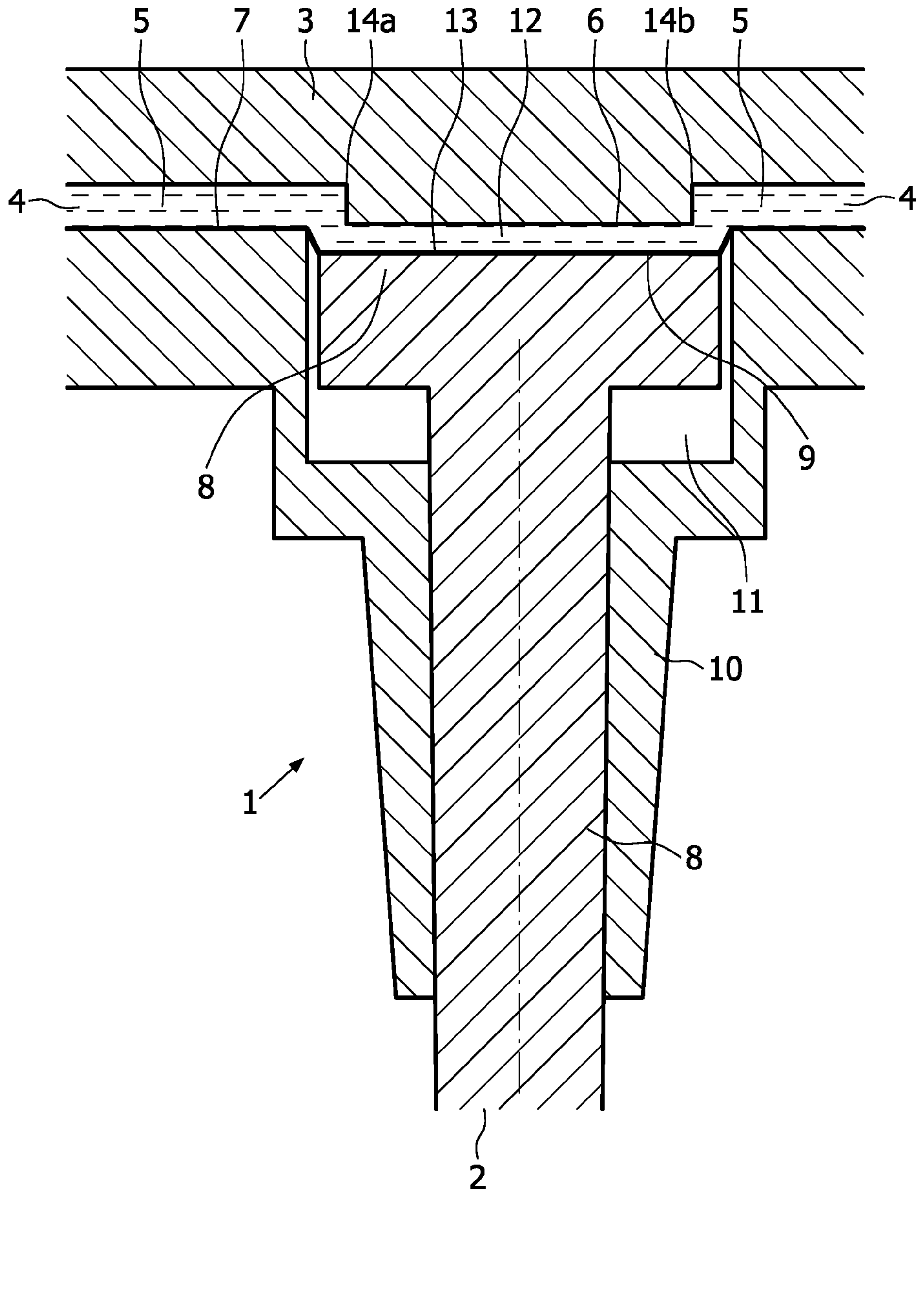
FIG. 4 is a sectional side view of a substrate with an open valve of a valve/pump unit according to the present invention, wherein the upper surface of the actuating element overlaps the end parts of two faced micro channels.

FIG. 4 shows a micro fluidic device 1 according to FIG. 2 with the difference that the upper surface of the actuating element 8 overlaps the end parts 14*a*/14*b* of two micro channels, which are connected via a temporally formable channel 12 formed by the flexible membrane 7 on the substrate 3 to admit a through going fluid flow along the valve area 6 of the substrate 3.

Figure 5:
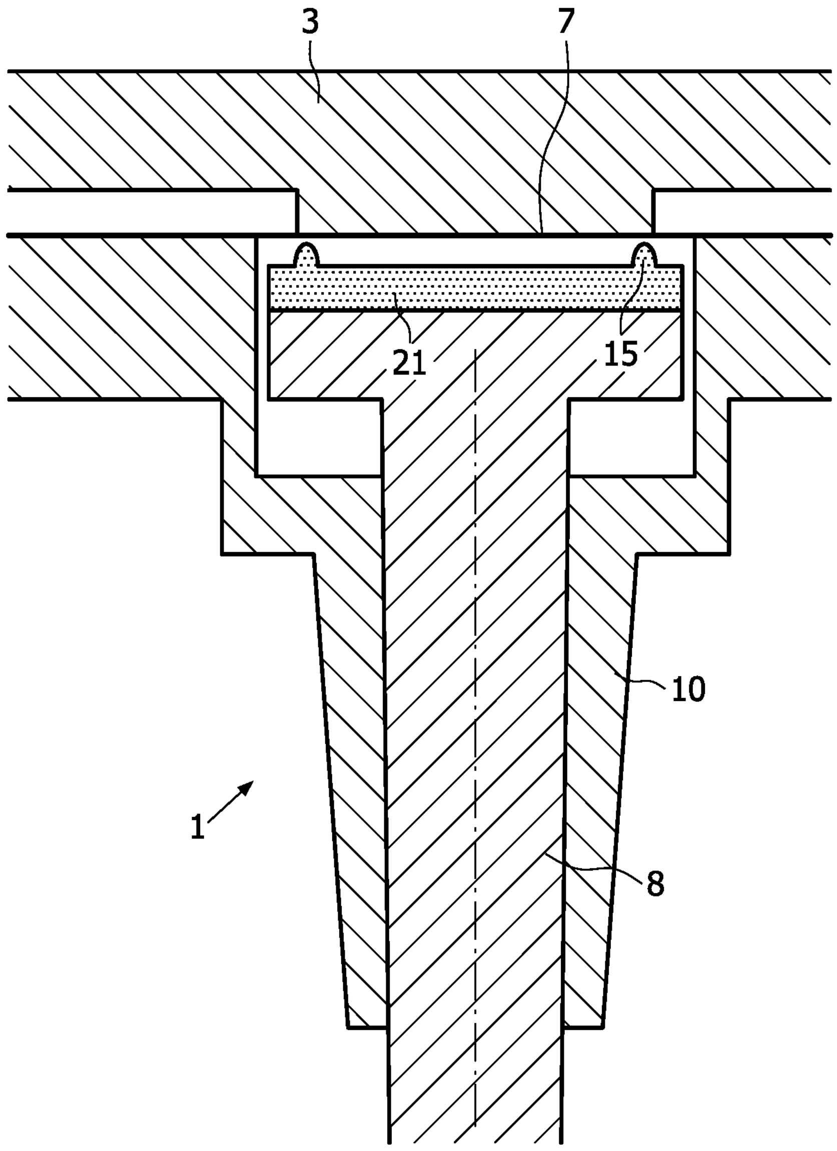
FIG. 5 is a sectional side view of a substrate with a closed valve of a valve/pump unit according to the present invention, wherein a collar is arranged on the upper surface of the actuating element.

FIG. 5 shows a micro fluidic device 1 according to FIG. 4 with the difference that the valve/pump unit 2 is in a closed state and the upper surface section 21 of the actuating element 8 facing the membrane 7 comprises a collar 15 functions as a sealing ring. Further, the upper surface section 21 is of a different flexible material.

Figure 6:
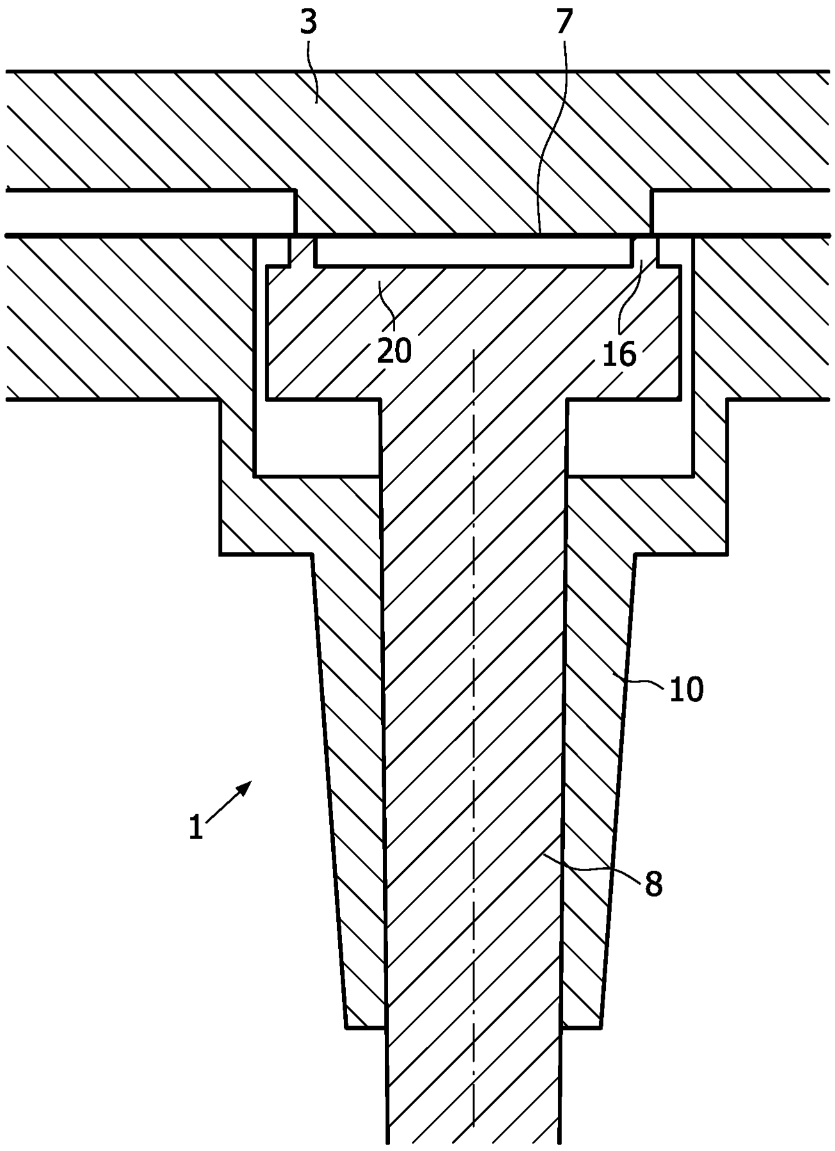
FIG. 6 is a sectional side view of a substrate with a closed valve of a valve/pump unit according to the present invention, wherein two bars are arranged on the upper surface of the actuating element.

FIG. 6 shows a micro fluidic device 1 according to FIG. 5 with the difference that the collar 15 functions as a sealing ring is replaced with a bar 16 at the bottom part 20.

Figure 7:
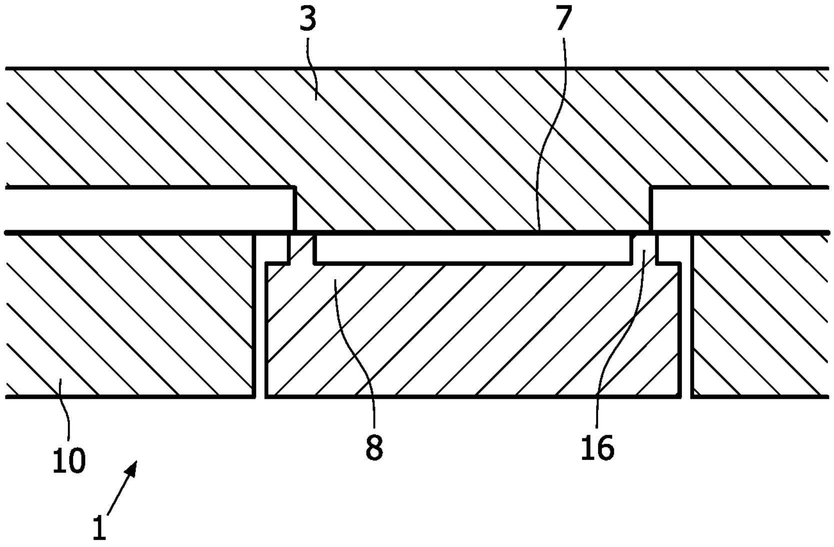
FIG. 7 is a sectional side view of a substrate with a closed valve of a valve/pump unit according to the present invention, wherein a collar is arranged on the upper surface of the actuating element.

FIG. 7 shows a micro fluidic device 1 according to FIG. 6 with the difference that the actuating element 8 has no shaft. This type of actuating element provides a flat design for the actuating element 8. However, instead of a bar 16 the actuating element 8 can comprise a collar 15 at the bottom part. Further, it is preferred that the actuating element 8 comprising a collar 15 or a bar 16 is one part and of the same flexible material.

Figure 8:
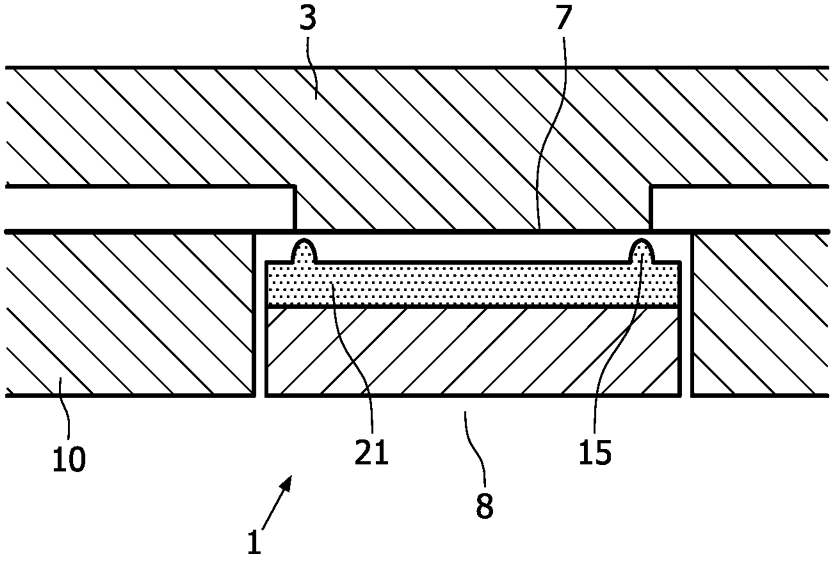
FIG. 8 is a sectional side view of a substrate with a closed valve of a valve/pump unit according to the present invention, wherein two bars are arranged on the upper surface of the actuating element.

FIG. 8 shows a micro fluidic device 1 according to FIG. 7 with the difference that the actuating element 8 facing the membrane 7 comprises a collar 15 functions as a sealing ring instead of a bar 16 at the bottom part and the upper surface section 21 is of a different flexible material.

Figure 9:
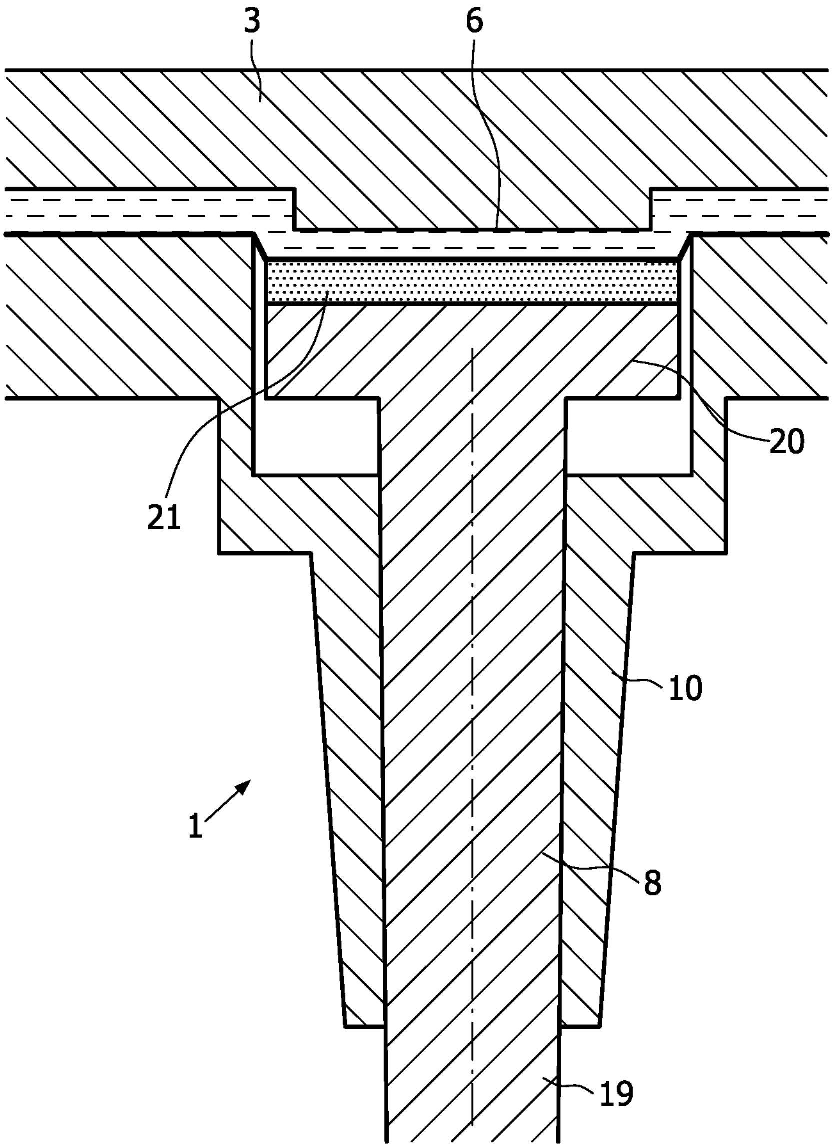
FIG. 9 is a sectional side view of a substrate with an open valve of a valve/pump unit according to the present invention, wherein the upper surface of the actuating element is covered with an elastic material layer.

FIG. 9 shows a micro fluidic device 1 with an actuating element comprising a shaft 19 and a bottom part 20. The diameter of the bottom part 20 is larger than the diameter of the shaft 19. FIG. 9 differs from FIG. 2 in that the upper surface of the bottom part 20 is covered with an elastic material layer 21.

Figure 10:
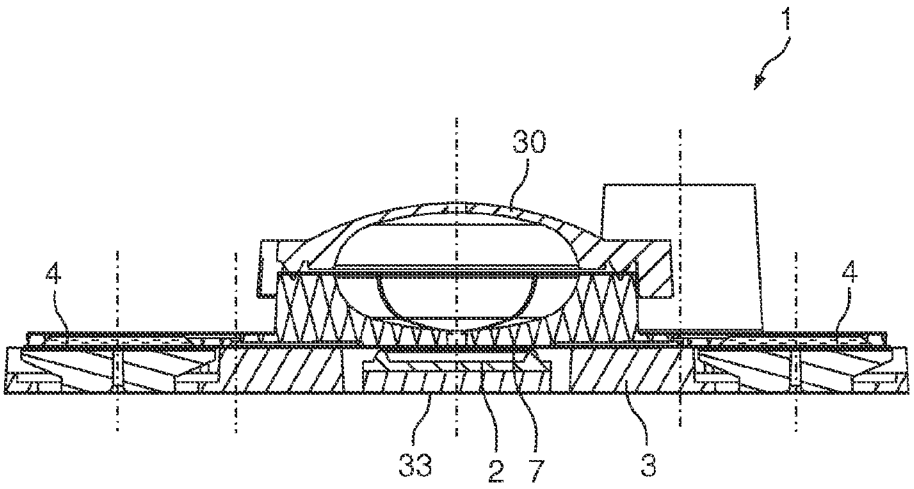
FIG. 10 is a sectional view of a substrate including a fluid chamber with an open valve of a valve/pump unit according to the present invention.
Figure 11:
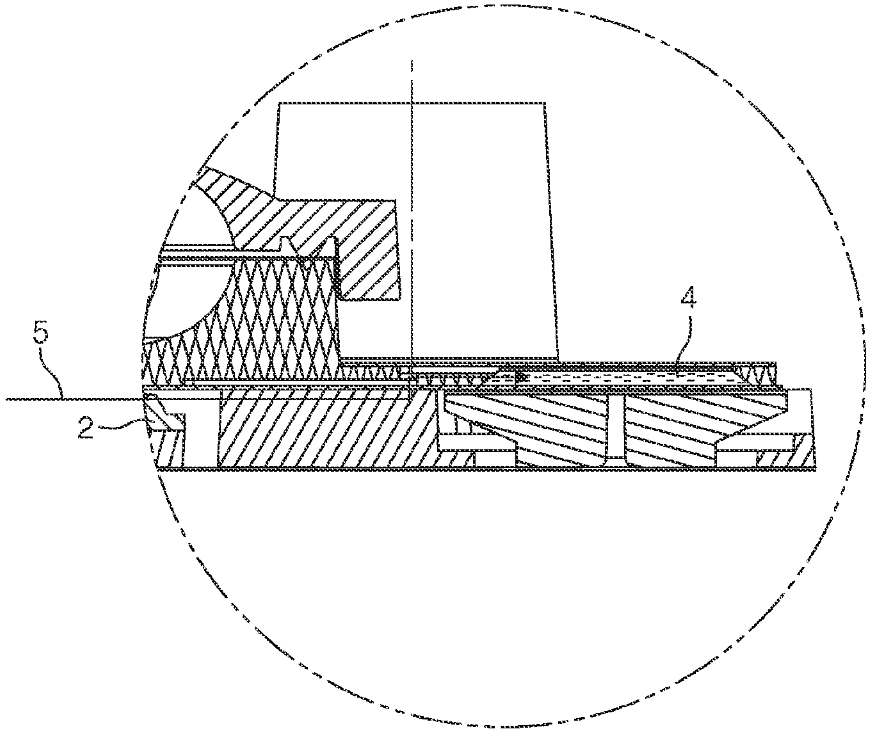
FIG. 11 is an exploded view of FIG. 10.

FIG. 10 shows a micro fluidic device 1 with a substrate 3 including a fluid chamber 30 and a plurality of micro channels (4), out of which only two are shown in this figure. FIG. 11 is an exploded view of the micro fluidic channel of FIG. 10. The sample fluid (5) is directed from one micro channel (4) to plurality of micro channels (4) via the valve area (6). The fluid chamber is in the valve area (6). The fluid chamber (30) is arranged to store the sample fluid (5). The flexible membrane (7) is arranged to form a lower surface of the fluid chamber. The valve/pump unit (2) is attached to a flexible foil (33). The flexible foil (33) is capable of aligning the valve/pump unit (2) to the lower surface of the substrate when the actuating element (8) is moved towards the lower surface of the substrate.

Figure 12:
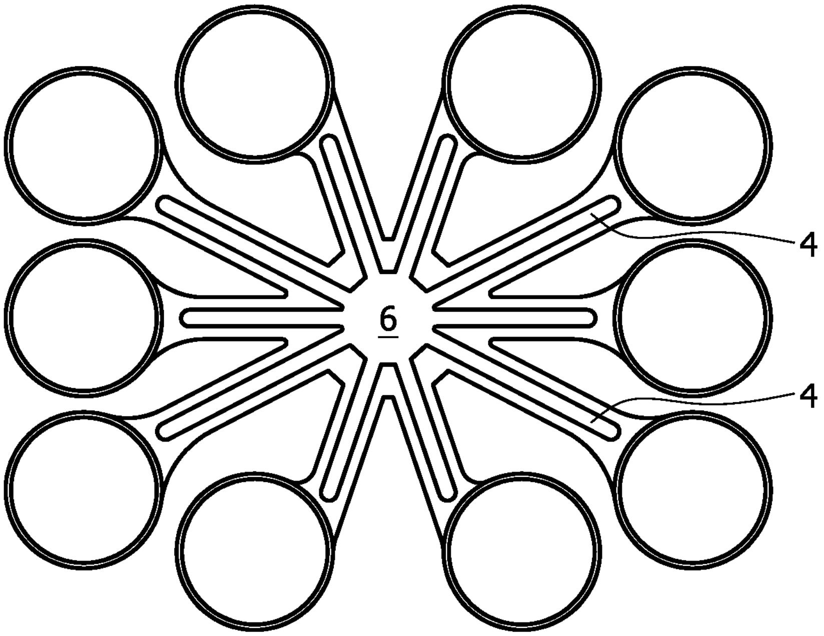
FIG. 12 is a plan view of a micro fluidic device including multiple micro channels.

FIG. 12 shows a plurality of micro channels (4) those are aligned radially and start from a bottom of the lower surface of the substrate (3) from centre passing the valve area and cross to a top of the lower surface of the substrate.

The substrate material can be selected from the group comprising glass, ceramic, silicon, metal and/or polymer.

According to the present invention, the substrate surface can be at least partly covered with a polymeric layer. The micro channel structure can be formed in said polymer layer by general known techniques. For example, micro channels can be formed by use of laser ablation techniques. A laser ablation process can be used, because it avoids problems encountered with micro lithographic isotropic etching techniques which may undercut masking during etching, giving rise to asymmetrical structures having curved side walls and flat bottoms. The use of laser-ablation processes to form microstructures in substrates such as polymers increases simplicity of fabrication, thus lowers manufacturing costs. However, injection molding may also be used as a suitable fabrication method.

On top of the substrate a flexible membrane is arranged. The size of the flexible membrane may be selected so that the flexible membrane completely or partly covers the upper surface of the substrate. It can be preferred also that the flexible membrane wrappers the substrate. It is most preferred that the flexible membrane covers the fluid sample transport device at least on all areas where a pump or valve action is desired and/or a temporally channel 12 needs to be formed for directing the fluid sample to a cavity or area, where the fluid sample is detected, controlled and/or processed. It can be further preferred that the flexible membrane covers the processing, controlling and/or detecting areas as well. However, it is most preferred that the flexible membrane completely covers or wrappers the upper surface of the substrate.

FIGS. 1 to 6 and 9 shows a micro fluidic device 1 in a sectional side view of a substrate with a valve/pump unit according to the present invention, wherein the actuating element has a cylindrical shaft and a cylindrical bottom part and the bottom part has a larger diameter than the shaft. However, as can be seen from FIGS. 7 and 8 the actuating element can have a flat design, i.e. a bottom part, preferably a cylindrical bottom part, and no shaft. Such an actuating element can be actuated for example by finger pressure or suchlike. Further, as shown in FIGS. 10-11, the actuating element has a cylindrical bottom part without a shaft. The valve/pump unit is attached to the flexible foil 33.

The membrane as used according to the present invention is liquid tight, so that the fluid does not penetrate the membrane during operation. It may be preferred that the membrane is flexible and/or elastic in order to form and reform a temporally micro channel.

Suitable membrane materials are polymers, preferably natural or synthetic rubbers. Since metal foils or metal membranes are not elastic, metal foils or metal membranes can be excluded as a membrane material. Also preferred membrane materials are thermoplastics, elastomers, thermoplastic elastomers and silicones as well as mixtures thereof.

A preferred temporally formed channel can have a U-like profile through which a fluid flow can temporally be directed.

The depth of the temporally formed channels can be of 10 μm to 5000 μm, preferably 20 μm to 500 μm and more preferably 30 μm to 200 μm.

To obtain a good pump and/or valve effect of the membrane it may be preferred that the membrane has a thickness of 1 μm to 1000 μm, preferably 20 μm to 200 μm and more preferably 50 μm to 100 μm. If the membrane is too thin there is a danger of deterioration of the membrane, which may result in leakage of the fluid sample. However, if the membrane is too thick, there is a danger of malfunction of the pump and/or valve effect of said membrane with respect to fluid transportation. Most preferred is a rubber membrane having a thickness between 50 micron and 200 micron.

In order to achieve an improved pump and valve action it can be preferred that the flexible membrane posses an e-modulus of 0.5 Mpa to 250 Mpa, preferably of 1 Mpa to 100 Mpa and more preferred of 5 Mpa to 10 Mpa.

Further, it may be preferred that the flexible membrane has an elastic deformation of at least 105% and preferably of at least 110%. This material feature may have an advantage with respect to facilitate the formation of a temporally channel.

The cover element can be a cartridge that can be removable mounted to the membrane-covered substrate. Preferably, the cover element is a cartridge or an integral part of an apparatus for chemical, diagnostic, medical and/or biological analysis.

The cover element comprises at least one through going cut-out for receiving an actuating element. The through going cut-out is designed such that it allows an up- and down-movement of the actuating element. Further, the through going cut-out comprises a chamber that is released at a movement of the actuating element opposite to the lower surface of the membrane into which the flexible membrane can engage to form a temporal channel.

According to a preferred embodiment of the present invention, the upper part of the through going cut-out of the cover element has the form of a chamber to receive the bottom part and the lower part of the through going cut-out of the cover element has a smaller cylindrical form to receive the shaft part of the actuating element.

The actuating element can be made of plastic, metal, glass and/or ceramic material. Preferably, the actuating element is a plunger.

According to a preferred embodiment, the actuating element has a shaft and a bottom part 20 having a larger diameter than the shaft.

According to a further preferred embodiment of the present invention, the upper surface of the bottom part is covered with an elastic material layer.

The upper surface of the actuating element can be mounted to the membrane. However, it is not necessary that the actuating element is mounted to the membrane. In this case, a temporally membrane channel can be formed for example, if fluid is subjected to an external pressure.

According to a preferred embodiment of the actuating element, the upper surface of the actuating element completely covers the valve area.

However, it is more preferred that the upper surface of the actuating element overlaps the end parts of two micro channels, which are connected via a temporally formable channel formed by the flexible membrane on the substrate to admit a through going fluid flow. This embodiment of an actuating element reduces the dead volume of the valve/pump unit to about zero, since due to the overlap of the upper surface of the actuating element all fluid can be returned from the valve area into the micro channel system of the substrate.

The upper surface of the actuating element can comprise a collar and/or bar. The collar and/or bar can have a sealing function, so that fluid cannot creep between the valve area and the flexible membrane, when the valve is in a closed state. To increase the sealing function of the collar and/or bar it can be preferred that the collar and/or bar partly engages into the contacting micro channels.

Further, the collar and/or bar may have a pump action. For example, if the diameter of the collar is smaller as the diameter of the valve area, movement of the actuating element up and down causes a suction or press action. Thus, the actuating element can be a thin flexible material with a collar and/or bar. Such an actuating element can be actuated for example by finger pressure.

The micro fluidic device according to the present invention can comprise at least one processing, controlling and/or detecting element. The micro fluidic device according to the present invention can be used for:

chemical, diagnostic, medical and/or biological analysis, comprising assays of biological fluids such as egg yolk, blood, serum and/or plasma;

environmental analysis, comprising analysis of water, dissolved soil extracts and dissolved plant extracts;

reaction solutions, dispersions and/or formulation analysis, comprising analysis in chemical production, in particular dye solutions or reaction solutions; and/or quality safeguarding analysis.

The invention claimed is:

1. A micro fluidic device comprising at least one valve/pump-unit, wherein the micro fluid device comprises:

a substrate, wherein on a lower surface of said substrate at least two micro channels are arranged to direct a fluid sample flow on the substrate, whereby said at least two micro channels are disconnected by a valve area on the lower surface of said substrate, wherein the valve area includes a protrusion of the substrate that separates the at least two micro channels, wherein the at least two micro channels and the protrusion are located in a one plane;

at least one flexible membrane, wherein the flexible membrane is arranged on the lower surface of said substrate;

an actuating element with an upper surface for contacting the flexible membrane; and at least one cover element arranged on a lower surface of the flexible membrane, wherein the cover element comprises at least one through going cut-out for receiving the actuating element, so that movement of said actuating element causes a movement of the flexible membrane to cause or stop a directed fluid flow on said substrate, and so that a fluid flow between said at least two micro channels is directed among the valve area of the lower surface of the substrate and the upper surface of the flexible membrane through a temporarily formable channel formed by the flexible membrane covering the valve area, wherein a movement of the actuating element towards the protrusion of the lower surface of the substrate causes a valve action to stop the fluid flow between the at least two micro channels and a movement opposite to the lower surface of the substrate releases a space in a chamber into which the flexible membrane can engage to form the temporarily channel and the upper surface of the actuating element covers at least partly the membrane surface at valve area, wherein the valve area includes a fluid chamber to store the sample fluid and the sample fluid is dispensed through different micro channels.

2. The micro fluidic device according to claim 1, wherein the flexible membrane is capable of aligning the actuating element to the lower surface of the substrate when the actuating element is moved towards the lower surface of the substrate.

3. A micro fluidic device comprising at least one valve/pump-unit, wherein the micro fluid device comprises:

a substrate, wherein on a lower surface of said substrate at least two micro channels are arranged to direct a fluid sample flow on the substrate, whereby said at least two micro channels are disconnected by a valve area of said substrate, wherein the valve area includes a protrusion of the substrate that separates the at least two micro channels, wherein the at least two micro channels and the protrusion are located in a one plane;

at least one flexible membrane, wherein the flexible membrane is arranged on the lower surface of said substrate;

an actuating element with an upper surface for contacting the flexible membrane;

at least one cover element arranged on a lower surface of the flexible membrane, wherein the cover element comprises at least one through going cut-out for receiving the actuating element, so that movement of said actuating element causes a movement of the flexible membrane to cause or stop a directed fluid flow on said substrate, and so that a fluid flow between said at least two micro channels is directed among the valve area of the lower surface of the substrate and the upper surface of the flexible membrane through a temporarily formable channel formed by the flexible membrane covering the valve area, wherein a movement of the actuating element towards to the lower surface of the substrate causes a valve action and a movement opposite to the lower surface of the substrate releases a space in a chamber into which the flexible membrane can engage to form the temporary channel and the upper surface of the actuating element covers at least partly the membrane surface at the valve area, wherein the micro channels are aligned radially and start from a center portion of a bottom of the lower surface of the substrate passing the valve area and crossing to a top of the lower surface of the substrate, wherein the valve area includes a fluid chamber to store the sample fluid and the sample fluid is dispensed through different micro channels.

4. The micro fluidic device according to claim 1, wherein the flexible membrane is arranged to form a lower surface of the fluid chamber.

5. The micro fluidic device according to claim 1, wherein the upper surface of the actuating element overlaps end parts of the at least two micro channels, which are connected via the temporarily formable channel formed by the flexible membrane on the substrate to admit a through going fluid flow.

6. The micro fluidic device according to claim 1, wherein the upper surface of the actuating element comprises a collar and/or bar.

7. The micro fluidic device according to claim 1, wherein the cover element is removably connected with the substrate, and wherein the cover element is a cartridge or an integral part of an apparatus for chemical, diagnostic, medical and/or biological analysis.

8. The micro fluidic device according to claim 1, wherein the actuating element has a shaft and a bottom part, wherein the bottom part has the upper surface for contacting the flexible membrane, and wherein the bottom part has a larger diameter than the shaft.

9. The micro fluidic device according to claim 1, wherein an upper surface of the bottom part is covered with an elastic material layer.

10. The micro fluidic device according to claim 1, wherein an upper part of the through going cut-out of the cover element has a form of a chamber to receive the bottom part and the lower part of the through going cut-out of the cover element has a smaller cylindrical form to receive a shaft part of the actuating element.

11. The micro fluidic device according to claim 1, wherein the flexible membrane has a thickness of 1 μm to 1000 μm.

12. The micro fluidic device according to claim 1, wherein the flexible membrane has an e-modulus of 0.5 Mpa to 250 Mpa; and/or the flexible membrane has an elastic deformation of at least 105%.

13. The micro fluidic device according to claim 1, wherein the micro fluidic device comprises at least one processing, controlling and/or detecting element.

14. The micro fluidic device of claim 1, wherein the flexible membrane has a thickness of 20 μm to 200 μm.

15. The micro fluidic device of claim 1, wherein the flexible membrane has a thickness of 50 μm to 100 μm.

16. The micro fluidic device of claim 1, wherein the flexible membrane has at least one of an e-modulus of 1 Mpa to 100 Mpa and an elastic deformation of at least 105%.

17. The micro fluidic device of 1, wherein the flexible membrane has at least one of an e-modulus of 5 Mpa to 10 Mpa and an elastic deformation of at least 110%.

18. The micro fluidic device of 1, wherein the upper surface of the actuating element covers exactly an outer surface of the valve area so that substantially all the fluid sample is returned from the valve area into the at least two micro channels when the actuating element is pressed against the protrusion of the lower surface of the substrate.

* * * * *